United States Patent
Haynes et al.

(10) Patent No.: US 10,591,420 B1
(45) Date of Patent: Mar. 17, 2020

(54) IN-LINE LASER PROFILOMETRY INSPECTION SYSTEM

(71) Applicant: SPIRIT AEROSYSTEMS, INC., Wichita, KS (US)

(72) Inventors: Mark Davis Haynes, Andover, KS (US); Glen Paul Cork, Wichita, KS (US)

(73) Assignee: Spirit AeroSystems, Inc., Wichita, KS (US)

(*) Notice: Subject to any disclaimer, the term of this patent is extended or adjusted under 35 U.S.C. 154(b) by 0 days.

(21) Appl. No.: 16/399,377

(22) Filed: Apr. 30, 2019

(51) Int. Cl.
| G01N 21/00 | (2006.01) |
| G01N 21/88 | (2006.01) |
| G01N 21/95 | (2006.01) |
| G01N 21/93 | (2006.01) |

(52) U.S. Cl.
CPC ......... *G01N 21/8806* (2013.01); *G01N 21/93* (2013.01); *G01N 21/9515* (2013.01); *G01N 2201/06113* (2013.01)

(58) Field of Classification Search
CPC .... G01J 3/02; G01J 3/513; G01J 3/51; G01N 15/1459; G01N 21/65

USPC .......................................................... 356/73
See application file for complete search history.

(56) References Cited

U.S. PATENT DOCUMENTS

| 2002/0166371 | A1* | 11/2002 | Ratti ........................ B60C 23/06 73/146 |
| 2006/0087305 | A1* | 4/2006 | Talanov .................. G01Q 60/22 324/71.1 |
| 2010/0172213 | A1* | 7/2010 | Qian ..................... H04R 23/002 367/140 |

* cited by examiner

*Primary Examiner* — Md M Rahman
(74) *Attorney, Agent, or Firm* — Hovey Williams LLP (57) ABSTRACT

An in-line laser profilometry inspection system broadly comprises a first laser, a first sensor, a second laser, a second sensor, a camera, a calibration standard, and an interface. The lasers transmit first and second light signals to a stringer charge or other part. The sensors detect the light signals reflecting off first and second edge walls of the part. The camera obtains a top-down image of the part. The calibration standard provides structure for calibrating the inspection system via the lasers and sensors. The interface allows a user to oversee part inspection. Data generated from the reflected light signals corresponding to a part profile may be analyzed based on at least first and second derivatives of the part profile such that the part is inspected during a cutting procedure.

20 Claims, 8 Drawing Sheets

IN-LINE LASER PROFILOMETRY INSPECTION SYSTEM

BACKGROUND

Ultrasonic cutting machines and other CNC machines are often used for making stringer charges and other precision-cut parts. Cuts made by these machines form edge walls that must conform to predetermined engineering standards and part designs. Despite the precise control of modern CNC machines, several factors may cause a CNC machine to make unacceptable cuts resulting in non-conforming edge walls. For example, a cutting knife or other end effector of the CNC machine may be dull, the CNC machine may be out of calibration, the CNC machine may be improperly programmed, or machine offsets and control parameters may be incorrect. Any of these factors may cause material gouging, fraying, chips, tears, inaccurate radiuses, edge wall angles, and part dimensions, and other edge wall non-conformances.

Edge wall non-conformances may not be discovered until a part is being assembled, resulting in significant rework and downtime during assembly. Identifying and mitigating the problem (or problems) causing non-conformances is more difficult if the non-conformances are not discovered immediately. Machine offsets and machine maintenance are sometimes used to address these problems, but they are typically only partial and/or temporary solutions.

SUMMARY

Embodiments of the present invention solve the above-mentioned problems and other related problems and provide a distinct advance in the art of part inspection systems. More particularly, the present invention provides a part inspection system that seamlessly integrates part inspection with part production to identify edge wall non-conformances in real time.

An embodiment of the invention is an in-line laser profilometry inspection system for inspecting a stringer charge being cut via an ultrasonic cutting machine. The inspection system broadly comprises a first laser, a first sensor, a second laser, a second sensor, a camera, a calibration standard, and a user interface in communication with a control system of the ultrasonic cutting machine.

The first laser is positioned on a left side of a laser mounting structure and transmits a first light signal to the stringer charge, which reflects off a first sidewall of the stringer charge. The first laser may be an ultraviolet laser or any other suitable laser source.

The first sensor is positioned on the left side of the laser mounting structure near the first laser and receives the reflected first light signal. The first sensor may be a laser displacement sensor or any other suitable sensor.

The second laser is positioned on a right side of the laser mounting structure and transmits a second light signal to the stringer charge, which reflects off a second sidewall of the stringer charge. The second laser may be an ultraviolet laser or any other suitable laser source.

The second sensor is positioned on the right side of the mounting structure near the second laser and receives the reflected second light signal. The second sensor may be a laser displacement sensor such as an Acuity brand AQ6-C300-288 model sensor or any other suitable sensor.

The camera is centered between the first laser and second laser and obtains a top-down image of the stringer charge. The camera may be a computer vision camera or any other suitable camera.

The calibration standard provides a structure for calibrating the part inspection system. An embodiment of the calibration standard is a composite step height standard including a first row of orthogonal steps and a second row of sloped steps. The calibration standard is mounted in a machine bed of the ultrasonic cutting machine and is shiftable between a stored position and a calibration position. For example, the calibration standard is stored in the machine bed during cutting operations and then rotated so that the orthogonal steps and sloped steps face the first laser and second laser during calibration.

The interface allows a user to oversee part inspection and includes a touchscreen display or other display for displaying a scrollable data table, a 3D part model window, a camera image feed, a status textbox, a status indicator, a plurality of virtual inputs, and a profile viewer window.

The scrollable data table includes a measurement results summary and in one embodiment shows centerline deviations, negative edge angles, positive edge angles, and total bottom widths. The scrollable data table may show nominal values, measured values, and differences between the nominal values and measured values (i.e., "deltas"). The scrollable data table may be color coded or may include other graphical features.

The 3D part model window includes a plurality of view inputs and shows a 3D part model and an overlay of measurement results from the scrollable data table. The view inputs allow a view of the 3D part model to be rotated, zoomed in and out, panned, centered, reset to a home position, or changed to perspective or orthogonal. The view inputs also allow a home position to be selected (such as the current view) and the overlay to be toggled on/off.

The camera image feed includes a top-down view of the stringer charge and in one embodiment captures a laser reflection line created by the first laser and second laser. A reference line may overlay the top-down view in alignment with the laser reflection line.

The status textbox includes status information of the most recently performed operation and in one embodiment displays info about the current part being processed and a summary of calibration results. The status indicator shows a current status or mode of the part inspection system and may include color codes, symbols, or other indications.

The virtual inputs include three buttons or any other suitable inputs for providing user control. For example, the virtual inputs may include an automation start/stop button, a manual control for allowing the user to manually set and change measurement values and/or load new parts, and a units toggle.

The profile viewer window includes an end-view graph of raw profile data and a number of virtual inputs. The profile viewer window is used for spot measurements, certification evaluation by metrology, and debugging. The virtual inputs include a scan button for instructing the inspection system to scan the stringer charge, a calibration check for initiating calibration via the calibration standard, and a recalibrate button for analyzing the current calibration and applying a new calibration to the inspection system.

The inspection system may be used simultaneously and in conjunction with the ultrasonic cutting machine. That is, the inspection system may perform part inspections and calibrations as the ultrasonic cutting machine is cutting the part or between intermittent cutting steps.

The part inspection system may be calibrated at any time, including before cutting or inspection begins. When a calibration is initiated, the calibration standard is shifted from a stored position to a calibration position. The first laser and second laser then transmit first and second laser signals to the calibration standard such that the first and second laser signals reflect off the orthogonal steps or sloped steps of the calibration standard to the first and second sensors. Data representative of a calibration target profile is then generated based on the reflected first and second laser signals. The calibration target profile data is then analyzed. Hardware or software adjustments may be made according to the calibration analysis.

The inspection system may perform a part inspection as follows. First, part information such as dimensional data and material data is received (such as via the user interface) and processed.

The first laser and second laser may then transmit signals to the part. Specifically, the first laser may transmit a first light signal to the part so that the first light signal reflects off a first sidewall of the part. Similarly, the second laser may transmit a second light signal to the part so that the second light signal reflects off the second sidewall of the part.

Data representative of a first portion of a part profile from the reflected first light signal and data representative of a second portion of the part profile from the reflected second light signal may then be generated. Left and right data limits may also be set. Outliers in the first portion and second portion data may be removed. The data may also be filtered to reduce or eliminate noise and/or to make the data more manageable.

Data representative of a first derivative of the first portion of the part profile and data representative of a first derivative of the second portion of the part profile is then generated. The first derivatives indicate sloping of the part profile portions but do not necessarily identify part sides without more information.

Data representative of a second derivative of the first portion of the part profile and data representative of a second derivative of the second portion of the part profile is then generated, The second derivatives indicate changes in slope of the part profile portions but do not necessarily identify beginning and ends of part sides without more information.

Peak points of inflection are then identified in the second derivatives. Rates of change in the first derivatives are then analyzed at the points corresponding to peak points of inflection in the second derivatives.

The first portion and second portion of the part profile are then matched to the key point locations. That is, data representative of the first sidewall of the first portion and data representative of the second sidewall of the second portion is determined according to the first derivative data and the second derivative data. Specifically, local maxima and local minima of the second derivatives that meet thresholds of acceptance in the first derivatives and the part profile identify critical features of detection such as sidewall edges, As such, the first sidewall and second sidewall (and other critical features) are identified over data noise and inconsequential profiles such as a butt-stop that follows along the part.

Data representative of a first sidewall angle and data representative of a second sidewall angle is then generated, Other sidewall data such as linearity or consistency may also be determined or generated.

Data representative of a first sidewall quality and data representative of a second sidewall quality is then generated according to the first sidewall angle and second sidewall angle or other sidewall data. This data may be numerical values such as a deviation or variation from a nominal or acceptable angle, linearity, or consistency, a qualitative descriptor such as "acceptable" or "unacceptable", or any other suitable data, Poorly cut parts will have burrs, frayed edges, or other irregularities that will cause large errors in the sidewall angle. As such, a numerical quantification of the cut quality may be obtained via the sidewall angle or other sidewall data.

The above steps are repeated several times as the part is being cut such that the entire part is inspected. The part profile analysis may also be simplified by obtaining key metrics from the part profile such as a width of the part, a centerline of the part, and a sidewall angle of each sidewall. A part trim profile may be derived from the centerline and width. A left trim profile may be expressed as the centerline minus half of the width, and a right trim profile may be expressed as the centerline plus half of the width. A combination of width, centerline, and edge wall angle(s) may fully quantify part trimming quality. For example, the edge wall angle provides a numerical quantification of cut quality. Poorly cut parts may have burrs, frayed edges, or other irregularities that will cause large error in the edge wall angle.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Embodiments of the present invention include a part inspection system that may be used with a computer-numerical-control (CNC) machine. The part inspection system will be discussed as a component of the CNC machine.

Turning to FIGS. 1-7, a CNC machine 10 constructed in accordance with an embodiment of the invention is illustrated. The CNC machine 10 is configured to cut and inspect a stringer charge 100 or other part.

Figure 1:
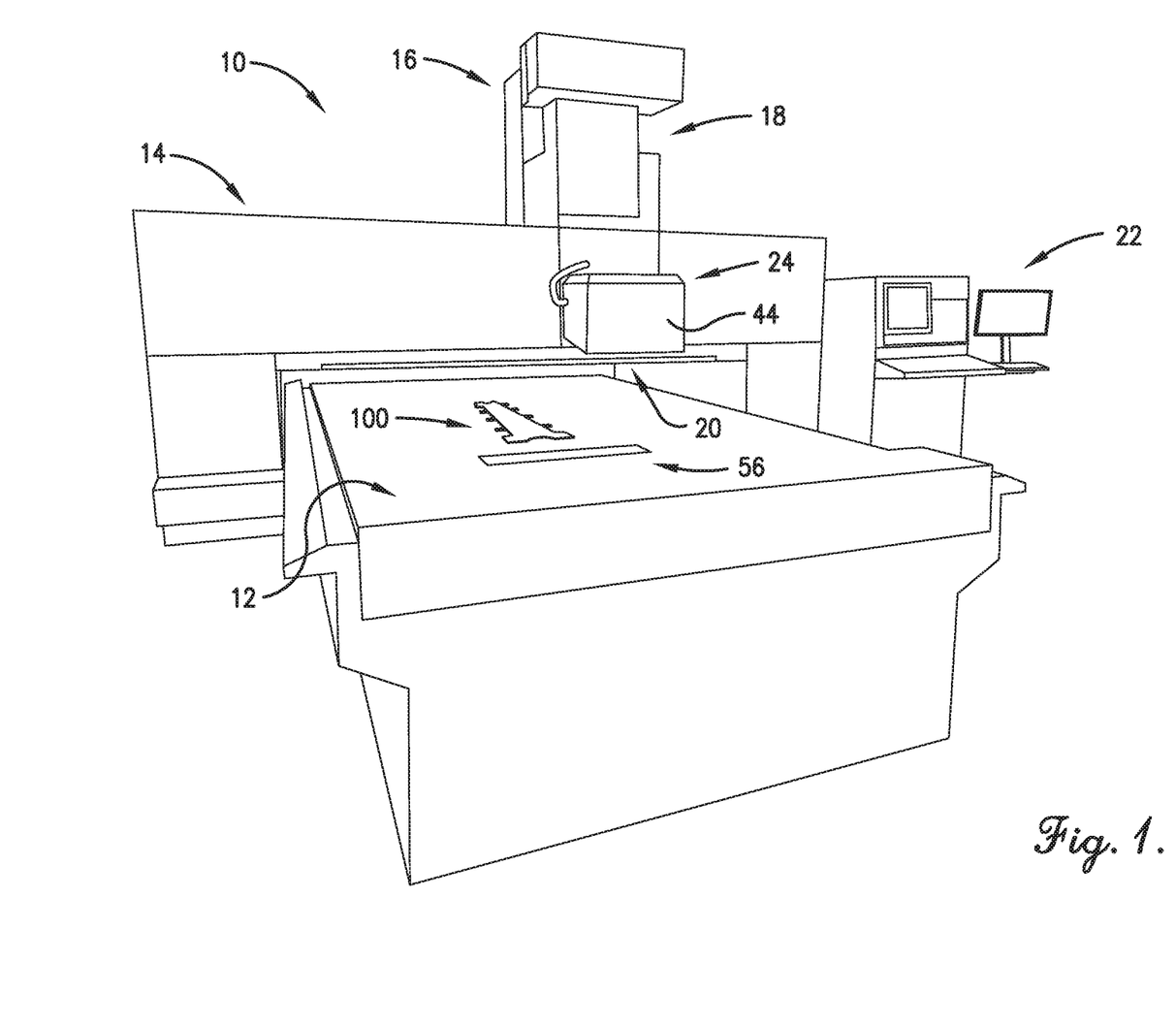
FIG. 1 is a perspective view of a CNC machine including a part inspection system in accordance with an embodiment of the invention.

The CNC machine 10 broadly comprises a machine bed 12, a gantry 14, a lateral axis carriage 16, a vertical axis carriage 18, a cutting implement 20, a control system 22, and a part inspection system 24. The CNC machine 10 may be a two dimension or three dimension (e.g., contouring) CNC system such as an ultrasonic cutting machine.

The machine bed 12 may be a large, flat, elongated base for supporting the stringer charge 100. The machine bed 12 may be entirely stationary or may include a conveyer or moveable portion.

The gantry 14 extends over the machine bed 12 and may include a longitudinal axis motor 26. The gantry 14 supports the lateral axis carriage 16 and the vertical axis carriage 18 and may include rails, tracks, or other structures for guiding the lateral axis carriage 16. The longitudinal axis motor 26 moves the gantry 14 along a longitudinal axis of the machine bed 12. The longitudinal axis motor 26 is controlled by longitudinal movement inputs from the control system 22 and may be a servomotor, a stepper motor, or the like.

The lateral axis carriage 16 may include a lateral axis motor 28 and supports the vertical axis carriage. The lateral axis motor 28 moves the vertical axis carriage 18 along the gantry 14 (and hence along the lateral axis of the machine bed 12). The lateral axis motor 28 is controlled by lateral movement inputs from the control system 22 and may be a servomotor, a stepper motor, or the like.

The vertical axis carriage 18 may include a vertical axis motor 30 and supports the cutting implement 20 and components of the part inspection system 24. The vertical axis motor 30 is controlled by vertical movement inputs from the control system 22 and may be a servomotor, a stepper motor, or the like.

The cutting implement 20 includes a cutting end effector for engaging the stringer charge 100. The cutting end effector may be a knife, a disc, a core sculptor, a router, a laser, a plasma cutter, a water jet or the like. In some embodiments, the cutting implement 20 may also include a cutting motor 32 controlled by cutting inputs from the control system 22 for vibrating, reciprocating, or rotating the cutting end effector.

Figure 5:
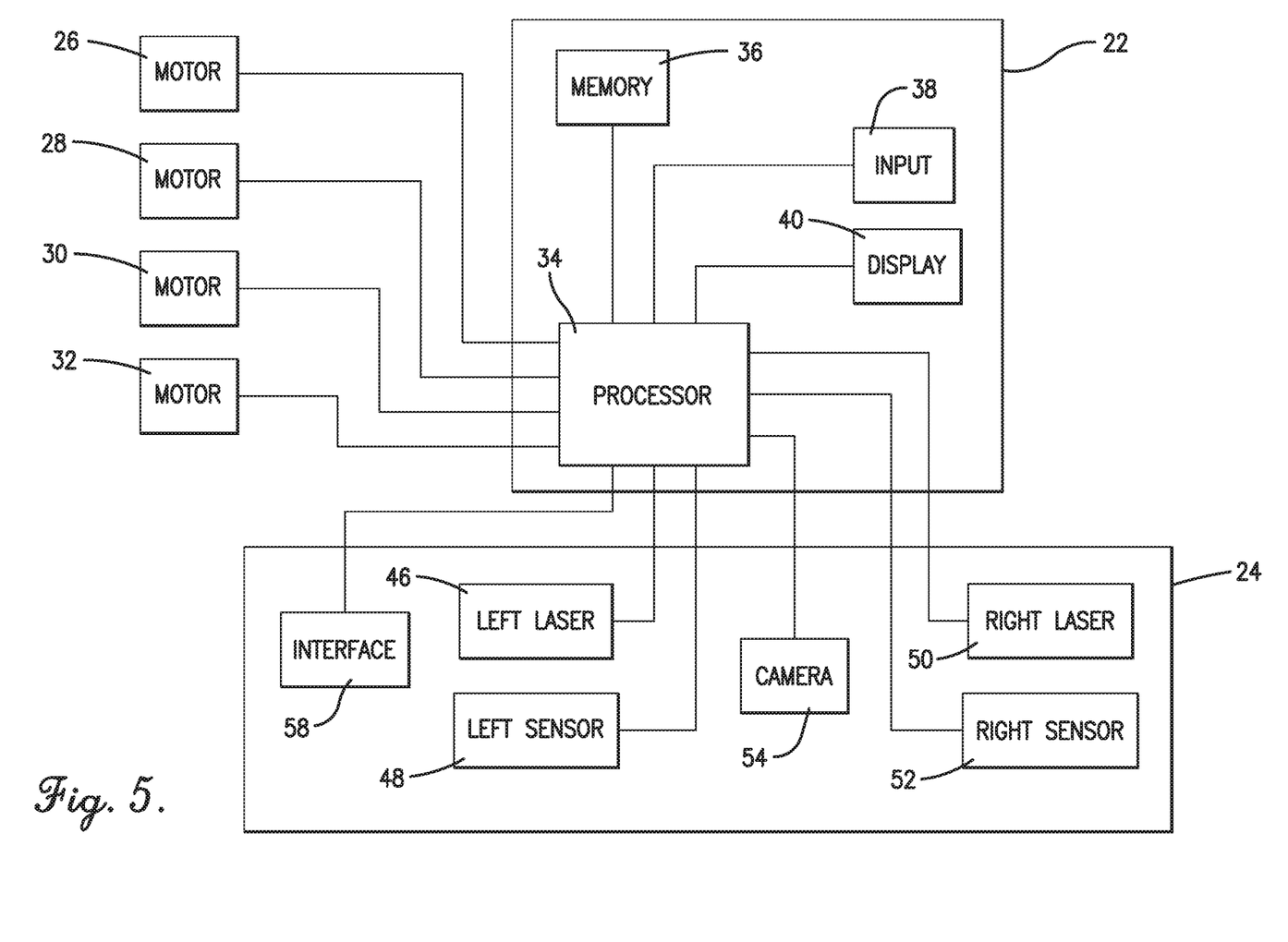
FIG. 5 is a schematic diagram of the part inspection system and a control system of the CNC machine of FIG. 1.

The control system 22 broadly comprises a processor 34, a memory 36, a plurality of inputs 38, and a display 40 and controls movement and activation of the cutting implement 20 and the part inspection system 24. The control system 22 may also include circuit boards and/or other electronic components such as a transceiver or external connection for communicating with external computing systems.

The processor 34 may implement aspects of the present invention with one or more computer programs stored in or on computer-readable medium residing on or accessible by the processor. Each computer program preferably comprises an ordered listing of executable instructions for implementing logical functions in the processor 34. Each computer program can be embodied in any non-transitory computer-readable medium, such as the memory 36 (described below), for use by or in connection with an instruction execution system, apparatus, or device, such as a computer-based system, processor-containing system, or other system that can fetch the instructions from the instruction execution system, apparatus, or device, and execute the instructions.

The memory 36 may be any computer-readable non-transitory medium that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The inputs 38 may comprise a keyboard, mouse, trackball, touchscreen, buttons, dials, virtual inputs, and/or a virtual reality simulator. The inputs 38 allow a user to activate and control the CNC machine 10 and part inspection system 24.

The display 40 may present virtual inputs, data spreadsheets and data tables, graphical data representations, computer models of the stringer charge 100, and other information. The display 40 may be a touchscreen, an LCD screen, an LED screen, and the like.

Figure 3:
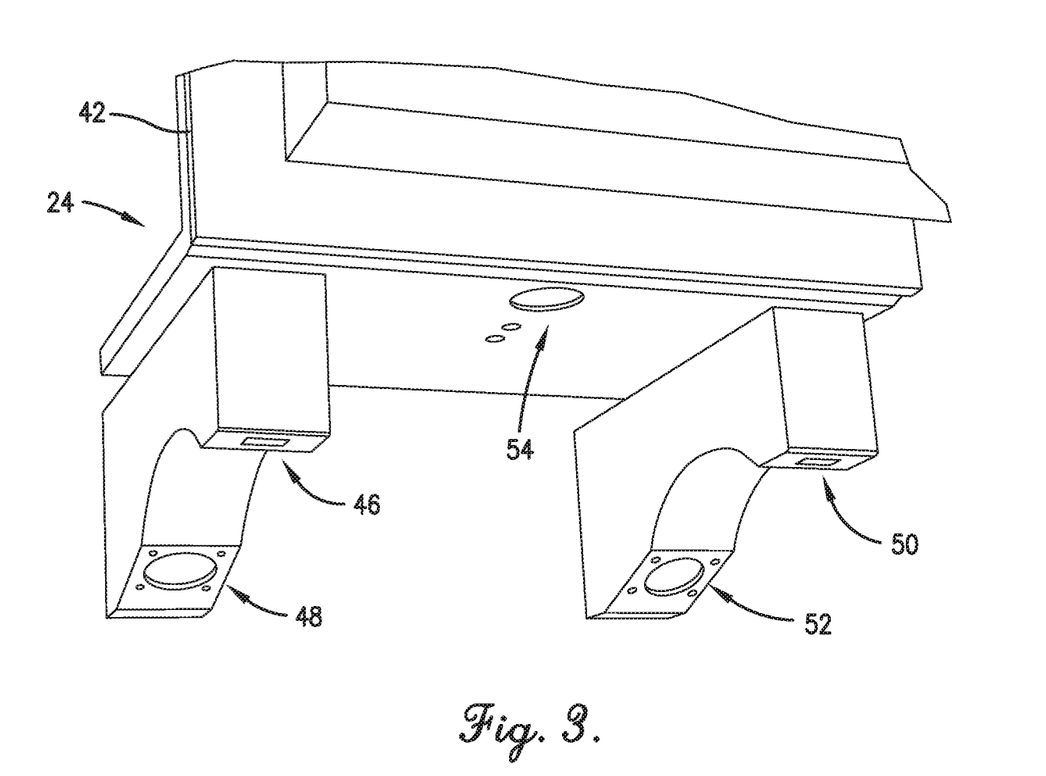
FIG. 3 is a bottom perspective view of the part inspection system of FIG. 1.

The part inspection system 24 broadly comprises a mounting structure 42, a housing 44, a first laser 46, a first sensor 48, a second laser 50, a second sensor 52, a camera 54, a calibration standard 56, and an interface 58. In an alternative embodiment, a single laser and a single sensor are used. In another embodiment, three or more lasers and/or three or more sensors are used. The part inspection system 24 verifies whether the stringer charge 100 is cut cleanly and may be integrated with the CNC machine 10 or may have a separate controller or control system in communication with the control system 22 described above.

The mounting structure 42 may include an L bracket, a flat plate, a mounting bus, or the like and may be formed of metal, plastic, composite material, or the like. The mounting structure 42 supports the first laser 46, first sensor 48, second laser 50, second sensor 52, and camera 54 on the vertical axis carriage 18.

The housing 44 encloses the first laser 46, first sensor 48, second laser 50, second sensor 52, and camera 54. The housing 44 protects these components from dust and debris such as particles resulting from cutting operations.

Figure 2:
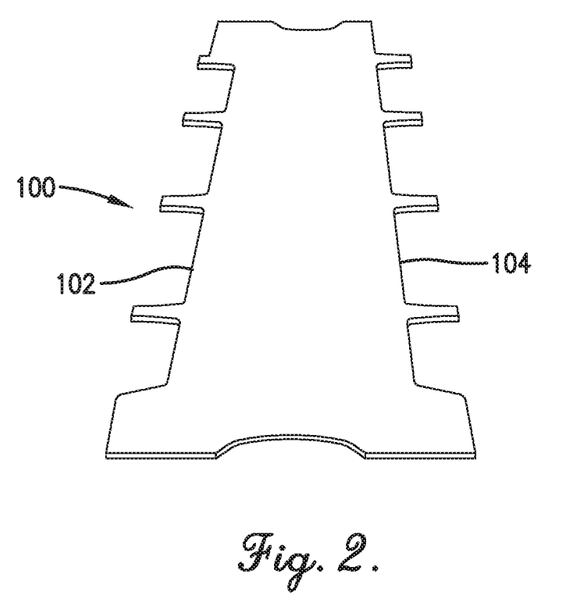
FIG. 2 is a perspective view of a stringer charge on which inspections may be performed in accordance with an embodiment of the invention.

The first laser 46 may be positioned on a left side of the mounting structure 42 and transmits a first light signal to the stringer charge 100. The first light signal reflects at least off a first sidewall 102 of the stringer charge 100. The first laser 46 may be an ultraviolet laser or any other suitable laser source.

The first sensor 48 may be positioned on the left side of the mounting structure 42 near the first laser 46 and receives the reflected first light signal. The first sensor 48 may be a laser displacement sensor such as an Acuity brand AQ6-C300-288 model sensor or any other suitable sensor.

The second laser 50 may be positioned on a right side of the mounting structure 42 and transmits a second light signal to the stringer charge 100. The second light signal reflects at least off a second sidewall 104 of the stringer charge 100. The second laser 50 may be an ultraviolet laser or any other suitable laser source.

The second sensor 52 may be positioned on the right side of the mounting structure 42 near the second laser 50 and receives the reflected second light signal. The second sensor 52 may be a laser displacement sensor such as an Acuity brand AQ6-C300-288 model sensor or any other suitable sensor.

The camera 54 may be centered between the first laser 46 and second laser 50 and obtains a top-down image of the stringer charge 100 (at least near a laser reflection line created by the first laser 46 and second laser 50). The camera 54 may be a computer vision camera such as an Allied Vision Mako G-131C model camera with an Edmund optics varifocal C-mount type lens.

Figure 4:
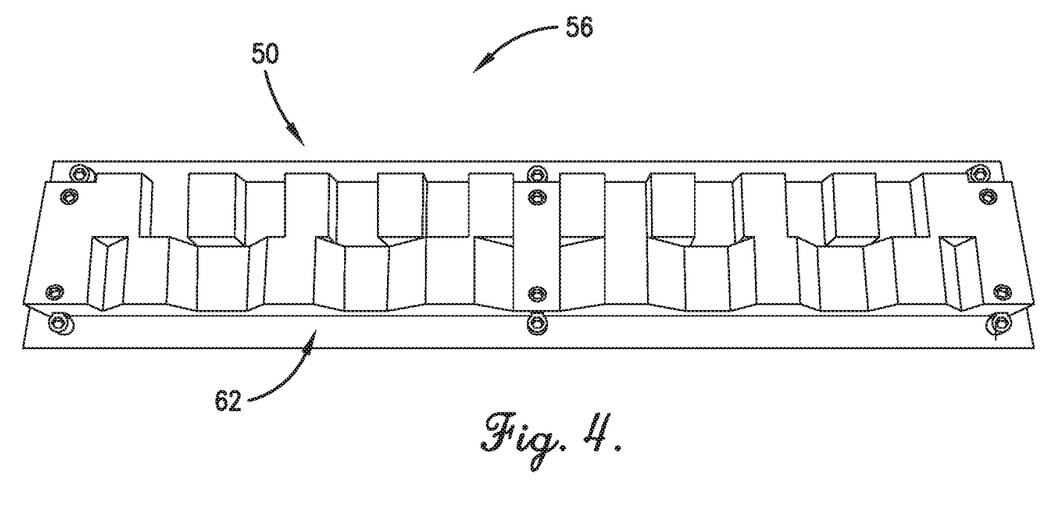
FIG. 4 is a perspective view of a calibration standard of the part inspection system of FIG. 1.

The calibration standard 56 may include a first row of orthogonal steps 60 and a second row of sloped steps 62 and may be a composite step height standard. The calibration standard 56 provides structure for calibrating the part inspection system 24. The calibration standard 56 may be pre-measured via a coordinate measuring machine (CMM), with a nominal definition of the calibration standard 56 being stored in a "config directory" in or accessible by the control system 22. The calibration standard 56 may be mounted in or on the machine bed 12 and may be shiftable between a stored position and a calibration position, For example, the calibration standard 56 may be stored in the machine bed 12 during cutting operations and then rotated so that the orthogonal steps 60 and sloped steps 62 face the first laser 46 and second laser 50 during calibration.

Figure 6:
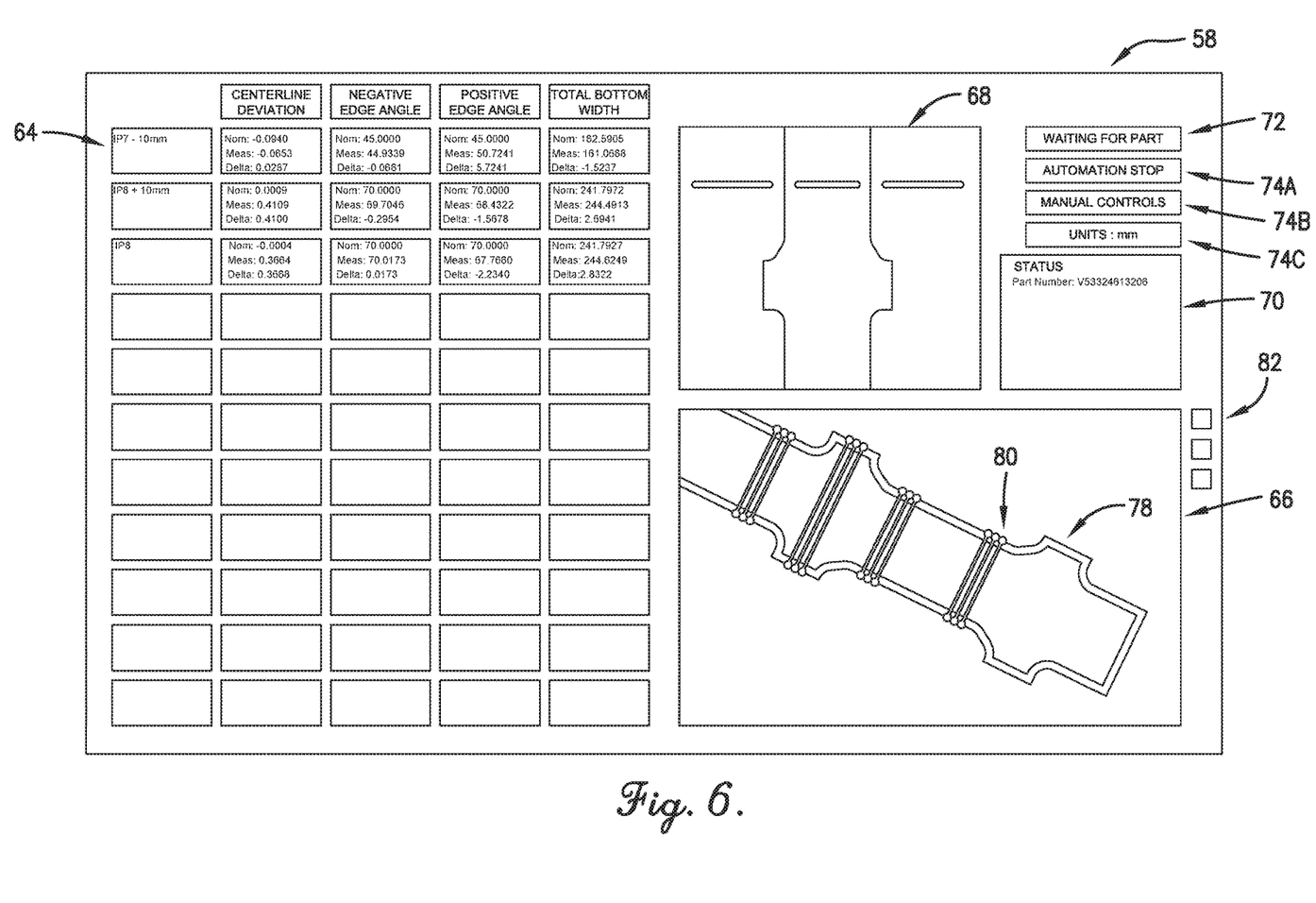
FIG. 6 is a screen view of a graphical user interface of the part inspection system of FIG. 1.

The interface 58 may include a touchscreen display or other display (such as display 22) and may include a scrollable data table 64, a 3D part model window 66, a camera image feed 68, a status textbox 70, a status indicator 72, a plurality of virtual inputs 74A-C, and a profile viewer window 76, The interface 58 allows a user to oversee part inspection.

The scrollable data table 64 summarizes measurement results and may show centerline deviations, negative edge angles, positive edge angles, and total bottom widths. The scrollable data table 64 may include nominal values, measured values, and differences between the nominal values and measured values (i.e., "deltas"). The scrollable data table 64 may be color coded or may include other graphical features.

The 3D part model window 66 may include a plurality of view inputs 82 and shows a 3D part model 78 and an overlay 80 of the measurement summary results from the scrollable data table 64. The view inputs 82 allow a view of the 3D part model 78 to be rotated, zoomed in and out, panned, centered, reset to a home position, or changed to perspective or orthogonal. The view inputs 82 also allow a home position to be selected (such as the current view) and the overlay 80 to be toggled on/off.

The camera image feed 68 includes a top-down view of the stringer charge 100 (at least near a laser reflection line created by the first laser 46 and second laser 50). A reference line may overlay the top-down view in alignment with the laser reflection line.

The status textbox 70 includes status information of the most recently performed operation. This may include info about the current part being processed and a summary of calibration results. The status indicator 72 shows a current status or mode of the part inspection system 24 and may include color codes, symbols, or other indications. For example, if the status indicator 72 is green, a part is currently being measured. If the status indicator 72 is yellow, the part inspection system 24 is waiting on the CNC machine 10 to communicate which part should be inspected next. If the status indicator 72 is red, the part inspection system 24 is turned off and will not perform any automated part inspection.

The virtual inputs 74A-C may include three buttons or any other suitable inputs for providing user control. Virtual input 74A may be an automation start/stop button. Virtual input 74B may be a manual control for allowing the user to manually set and change measurement values and/or load new parts. Virtual input 74C may be a units toggle. Additional inputs may be used without departing from the scope of the invention. When the first button is pressed, the part inspection system 24 will sit idle and wait for the CNC machine 10 to communicate the next part inspection. When the first button is pressed again, the part inspection system 24 will stop communicating with the CNC machine 10 and inspections of stringer charge profiles will stop.

Figure 7:
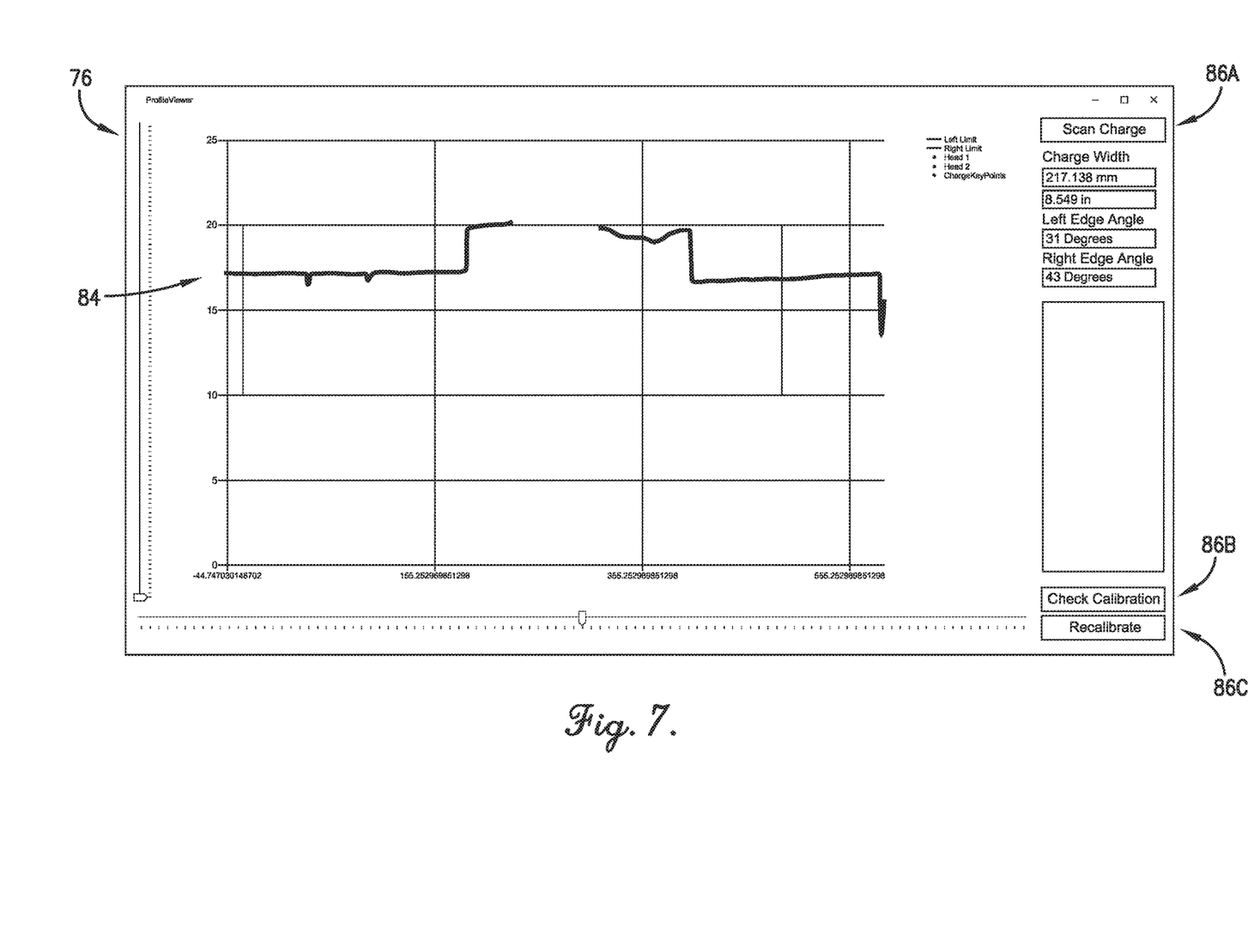
FIG. 7 is a screen view of a profile viewer window of the graphical user interface of FIG. 6.

The profile viewer window 76 includes an end-view graph 84 of raw profile data and a number of virtual inputs 86A-C (e.g., three buttons) for making spot measurements, certification evaluation by metrology, and debugging. Virtual input 86A may be a scan button for instructing the part inspection system 24 to scan the stringer charge 100. Virtual input 86B may be a calibration check for initiating calibration via the calibration standard 56. Virtual input 86C may be a recalibrate button for analyzing the current calibration and applying a new calibration to the part inspection system 24.

Figure 8:
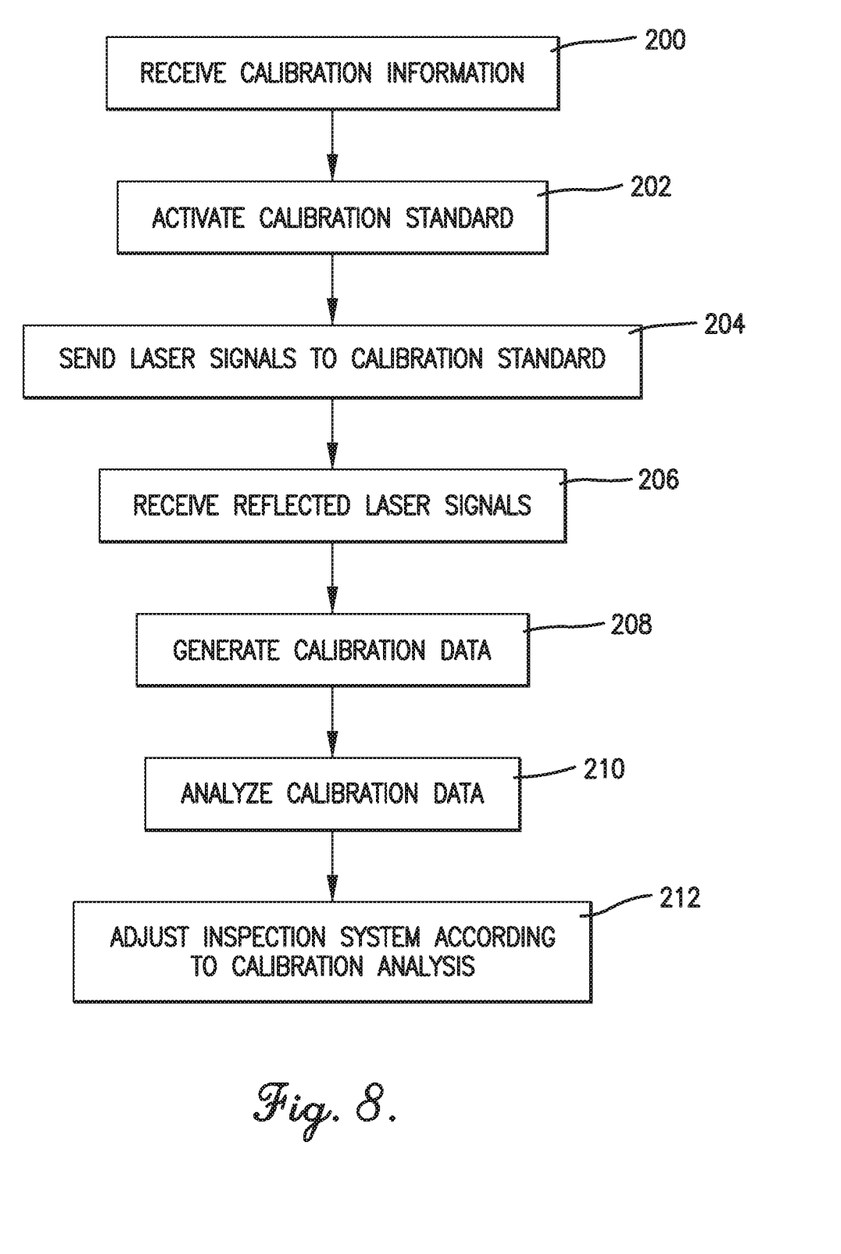
FIG. 8 is a flow diagram of method steps for calibrating the part inspection system of FIG. 1 in accordance with an embodiment of the invention.
Figure 9:
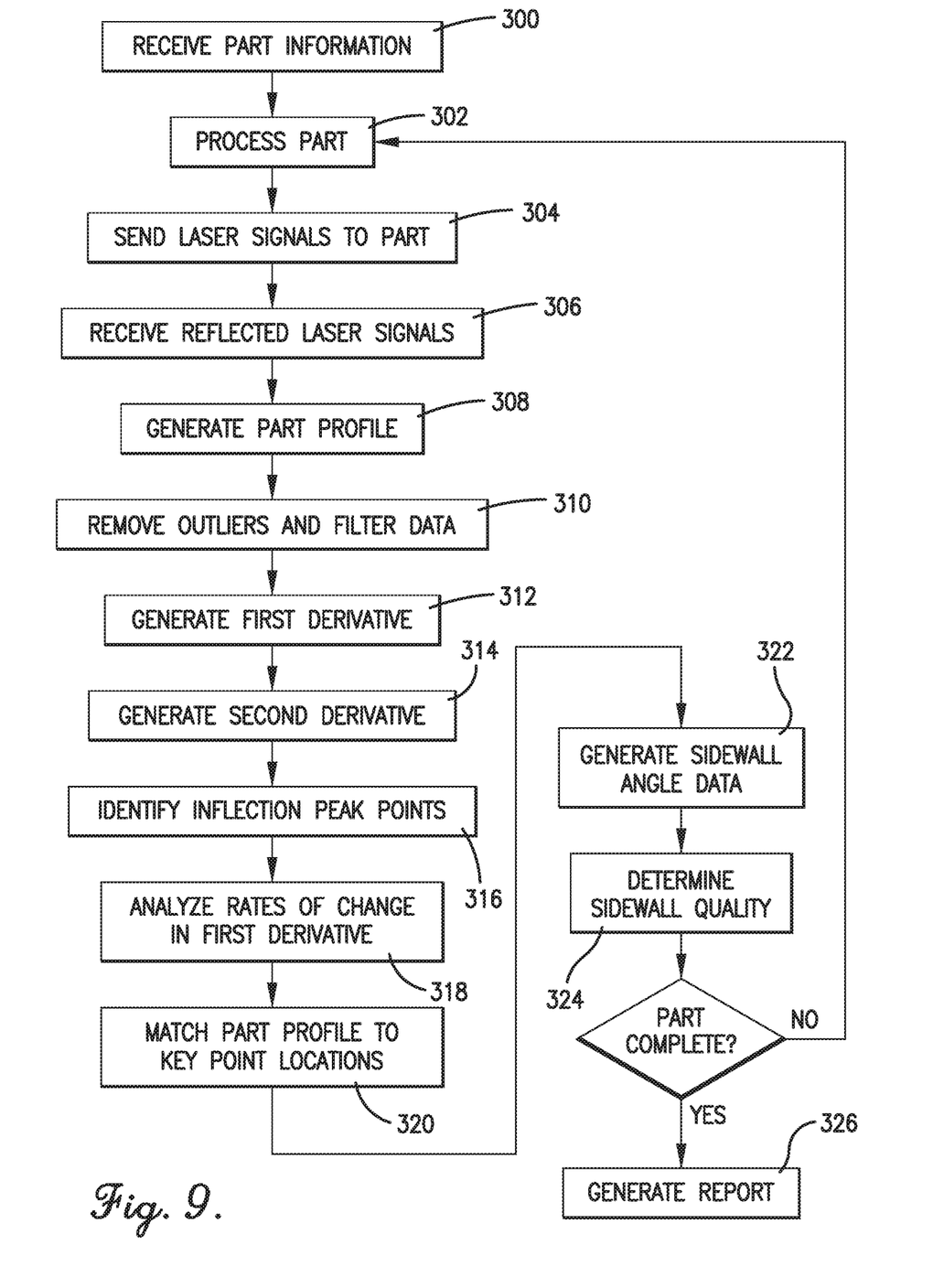
FIG. 9 is a flow diagram of method steps for inspecting a part in accordance with an embodiment of the invention.

Turning to FIGS. 8 and 9, use of the part inspection system 24 will now be described in detail. In an important aspect of the invention, the part inspection system 24 may be used simultaneously and/or in conjunction with the cutting implement 20. That is, the part inspection system 24 may perform part inspections and calibrations as the CNC machine 10 is cutting the stringer charge 100 or between intermittent cutting steps, the benefits of which will be described below.

Turning to FIG. 8, the part inspection system 24 may be calibrated at any time, including before cutting or inspection begins. In one embodiment, the part inspection 24 is calibrated during each program run prior to part inspection. To that end, the control system 22 or a user may instruct the part inspection system 24 to perform a calibration, as shown in block 200. For example, a user may select virtual input 86B to perform a calibration. The control system 22 may receive calibration information such as a type of calibration to be performed.

The calibration standard 56 may be shifted from a stored position to a calibration position, as shown in block 202. In one embodiment, the calibration standard 56 is stored in the machine bed 12 and presented from the machine bed 12 so that the part inspection system 24 can scan the calibration standard 56.

The part inspection system 24 may then perform a calibration. Specifically, the control system 22 may instruct the first laser 46 and second laser 50 to send first and second laser signals to the calibration standard 56, as shown in block 204. The first and second laser signals may reflect off the orthogonal steps 60 or sloped steps 62 of the calibration standard 56.

The control system 22 may then receive the reflected laser signals, as shown in block 206. The control system 22 may then generate data representative of a calibration target profile, as shown in block 208.

The control system 22 may then analyze the calibration target profile data, as shown in block 210. The control system 22 may then make hardware or software adjustments according to the calibration analysis, as shown in block 212.

The part inspection system 24 may perform a part inspection as follows. First, the control system 22 may receive part information, as shown in block 300. That is, the control system 22 may receive dimensional and material data of the stringer charge 100 such as in the form of 3D part model 78.

The control system 22 may then process the stringer charge 100, as shown in block 302. For example, the control system 22 may identify a location of the stringer charge 100 on the machine bed 12, a cutting progress or status of the CNC machine 10, and the like.

The first laser 46 and second laser 50 may then transmit signals to the stringer charge 100, as shown in block 304. Specifically, the control system 22 may instruct the first laser 46 to transmit a first light signal to the stringer charge 100 so that the first light signal reflects off the first sidewall 102 of the stringer charge 100. Similarly, the control system 22 may instruct the second laser 50 to transmit a second light signal to the stringer charge 100 so that the second light signal reflects off the second sidewall 104 of the stringer charge 100. The control system 22 may then receive the reflected first and second light signals via the first sensor 48 and the second sensor 52, as shown in block 306.

Data representative of a first portion of a part profile from the reflected first light signal and data representative of a second portion of the part profile from the reflected second light signal may then be generated, as shown in block 308. Left and right data limits may also be set. Data may be collected beyond these limits but not considered. An exemplary part profile graphical representation can best be seen in the profile dataset graph in FIG. 7.

Outliers in the first portion and second portion data may be removed, as shown in block 310. Data may also be filtered to reduce or eliminate noise and/or to make the data more manageable.

Data representative of a first derivative of the first portion of the part profile and data representative of a first derivative of the second portion of the part profile may then be generated, as show in block 312. The first derivatives indicate sloping of the part profile portions but do not necessarily identify part sides without more information.

Data representative of a second derivative of the first portion of the part profile and data representative of a second derivative of the second portion of the part profile may then be generated, as shown in block 314. The second derivatives indicate changes in slope of the part profile portions but do not necessarily identify beginning and ends of part sides without more information.

Peak points of inflection may then be identified in the second derivatives, as shown in block 316. Rates of change in the first derivatives may then be analyzed at the points corresponding to peak points of inflection in the second derivatives, as shown in block 318.

The first portion and second portion of the part profile may then be matched to key point locations, as shown in block 320. That is, data representative of the first sidewall 102 of the first portion and data representative of the second sidewall 104 of the second portion may be determined according to the first derivative data and the second derivative data. Specifically, local maxima and local minima of the second derivatives that meet thresholds of acceptance in the first derivatives and the part profile identify critical features of detection such as sidewall edges. As such, the first sidewall 102 and second sidewall 104 (and other critical features) are identified over data noise and inconsequential profiles such as a butt-stop that follows along the stringer charge 100.

Data representative of a first sidewall angle and data representative of a second sidewall angle may then be generated, as shown in block 322. Alternatively, other sidewall data such as linearity or consistency may be determined or generated.

Data representative of a first sidewall quality and data representative of a second sidewall quality may then be generated according to the first sidewall angle and second sidewall angle or other sidewall data, as shown in block 324. This data may be a numerical value such as a deviation or variation from a nominal or acceptable angle, linearity, or consistency, a qualitative descriptor such as "acceptable" or "unacceptable", or any other suitable data. Poorly cut parts may have burrs, frayed edges, or other irregularities that will cause large errors in the sidewall angle. As such, a numerical quantification of the cut quality may be obtained via the sidewall angle or other sidewall data.

Steps 302-324 may be repeated several times as the stringer charge 100 is being cut such that the entire stringer charge 100 may be inspected during cutting. Once the entire stringer charge 100 has been inspected or a desired inspection is complete, a report may be generated, as shown in block 326.

The above part profile analysis may be simplified by obtaining key metrics from the part profile. Specifically, a width of the part, a centerline of the part, and an sidewall angle of each sidewall may be obtained. A part trim profile may be derived from the centerline and width. A left trim profile may be expressed as the centerline minus half of the width. A left trim profile may be expressed as the centerline plus half of the width. A combination of width, centerline, and edge wall angle(s) may fully quantify part trimming quality. For example, the edge wall angle provides a numerical quantification of cut quality. Poorly cut parts may have burrs, frayed edges, or other irregularities that will cause large error in the edge wall angle.

The part inspection system 24 may be controlled via a numerical control program such as G-Code. To that end, the part inspection system 24 may be operated similar to a cutting end effector in terms of programming logic. Communication between the control system 22 and the part inspection system 24 may be a master-slave setup with unidirectional communication. The control system 22 may communicate commands for the part inspection system 24 to execute, if the part inspection system 24 undergoes electromechanical failure, the CNC machine 10 will not be prevented from completing execution of its numerical control program. This provides a failsafe for part production to continue if the part inspection system 24 is down for maintenance or repairs.

The numerical control program may implement a series of programmed M-codes. For example, several M-codes may be assigned part number definitions. Other M-codes may correspond to commands to fire lasers (with or without a dwell time), present and retract the calibration standard 56, and execute a calibration routine. Any other suitable M-code assignments and commands may also be used. The M-codes trigger or toggle relays between high and low states according to predetermined logic.

A user may program the part inspection system 24 via a master excel spreadsheet that defines a unique decimal number for each part. The decimal number may be communicated in binary over certain relays via their corresponding M-codes to the part inspection system 24. A machine output file may thus be generated. Depending on the number of stringers in the machine output file, a composite technician may need to reference several stringer edges in one program. The programmer may insert a comment so that the user knows when this is required. At the start of every program, it may be good practice to clear all relays and ensure that all parts are "complete" such that the inspection system 24 has a clean start.

The above-described part inspection system 24 provides several advantages. For example, the part inspection system 24 can be seamlessly integrated with a CNC machine and allows for automated in-line inspection with minimal impact to production workflow. The part inspection system 24 verifies that a part was cut cleanly, that the CNC machine is operating nominally, and that the NC program is creating a part that conforms to predetermined engineering standards and part design. The part inspection system 24 prevents defective parts from being passed downstream in production at the earliest possible opportunity. The part inspection system 24 uses inflection peak edge detection for real time geometric dimensional analysis and graphical overlay of measurement data on engineering 3D definition. The part inspection system 24 may obtain key metrics such as width, centerline, and edge wall angle to fully quantify part trimming quality without the need for full profile analysis.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for inspecting a part, the system comprising:
   a first laser that transmits a first light signal to the part so that the first light signal reflects off a first sidewall of the part;
   a first sensor that receives the reflected first light signal; and
   a controller communicatively coupled with the first laser and the first sensor, wherein the controller:
      generates first portion data representative of a first portion of a part profile from the reflected first light signal;
      generates first derivative data representative of a first derivative of the first portion from the first portion data;
      generates second derivative data representative of a second derivative of the first portion from the first derivative data;
      determines first sidewall data representative of the first sidewall from the first portion data according to the first derivative data and the second derivative data;
      generates first sidewall angle data representative of a first sidewall angle from the first sidewall data; and
      determines a first sidewall quality based on the first sidewall angle data.

2. The system of claim 1, further comprising a calibration standard, wherein the first laser further transmits the first light signal to the calibration standard so that the first light signal reflects off the calibration standard, the first sensor further receives the first light signal reflected off the calibration standard, and the controller further generates calibration data based on the first light signal reflected off the calibration standard and determines a calibration of the system based on the calibration data.

3. The system of claim 1, wherein the system operates in a subservient mode in conjunction with a CNC machine such that the CNC machine can continue operating if the system is offline or not operating normally.

4. The system of claim 1, further comprising:
   a second laser spaced from the first laser, wherein the second laser transmits a second light signal to the part so that the second light signal reflects off a second sidewall of the part; and
   a second sensor spaced from the first sensor, wherein the second sensor receives the reflected second light signal, wherein the controller further:
      generates second portion data representative of a second portion of the part profile from the reflected second light signal;
      generates first derivative data representative of a first derivative of the second portion from the second portion data;
      generates second derivative data representative of a second derivative of the second portion from the first derivative data of the second portion;
      determines second sidewall data representative of the second sidewall from the second portion data according to the first derivative data of the second portion and the second derivative data of the second portion;
      generates second sidewall angle data representative of a second sidewall angle from the second sidewall data; and
      determines a second sidewall quality based on the second sidewall angle data.

5. The system of claim 4, further comprising a camera positioned between the first laser and the second laser, wherein the camera creates a top-down image of the part.

6. The system of claim 4, wherein the controller further determines a centerline of the part and a width of the part so as to simplify determination of the first sidewall angle data and second sidewall angle data.

7. The system of claim 4, further comprising a calibration standard, wherein the first laser further transmits the first light signal to the calibration standard so that the first light signal reflects off the calibration standard, the first sensor further receives the first light signal reflected off the calibration standard, the second laser further transmits the second light signal to the calibration standard so that the second light signal reflects off the calibration standard, the second sensor further receives the second light signal reflected off the calibration standard, and the controller further generates calibration data based on the first light signal reflected off the calibration standard and the second light signal reflected off the calibration standard and determines a calibration of the system based on the calibration data.

8. The system of claim 7, the calibration standard being mountable to a part production bed and being shiftable between a stored position and a calibration position.

9. The system of claim 7, the calibration standard including a plurality of steps having a raised surface, left sidewalls, and right sidewalls.

10. The system of claim 9, some of the plurality of steps being arranged in a first row, the left and right sidewalls of the first row being orthogonal, and some of the plurality of steps being arranged in a second row, the left and right sidewalls of the second row being sloped.

11. A method of inspecting a part, the method comprising the steps of:
    transmitting a first light signal to the part via a first laser so that the first light signal reflects off a first sidewall of the part;
    receiving the reflected first light signal;
    generating first portion data representative of a first portion of a part profile from the reflected first light signal;
    generating first derivative data representative of a first derivative of the first portion from the first portion data;
    generating second derivative data representative of a second derivative of the first portion from the first derivative data;
    determining first sidewall data representative of the first sidewall from the first portion data according to the first derivative data and the second derivative data;
    generating first sidewall angle data representative of a first sidewall angle from the first sidewall data; and
    determining a first sidewall quality based on the first sidewall angle data.

12. The method of claim 11, further comprising performing the method steps as the part is being cut via a computer-numerical-control (CNC) machine.

13. The method of claim 11, further comprising the steps of:
    transmitting the first light signal to a calibration standard so that the first light signal reflects off the calibration standard;
    receiving the first light signal reflected off the calibration standard;
    generating calibration data based on the first light signal reflected off the calibration standard; and
    determining a calibration based on the calibration data.

14. The method of claim 13, further comprising the step of shifting the calibration standard from a stored position to a calibration position.

15. The method of claim 11, further comprising the steps of:
    transmitting a second light signal to the part from a second laser so that the second light signal reflects off a second sidewall of the part;
    receiving the reflected second light signal;
    generating second portion data representative of a second portion of the part profile from the reflected second light signal;
    generating first derivative data representative of a first derivative of the second portion from the second portion data;
    generating second derivative data representative of a second derivative of the second portion from the first derivative data of the second portion;
    determining second sidewall data representative of the second sidewall from the second portion data according to the first derivative data of the second portion and the second derivative data of the second portion;
    generating second sidewall angle data representative of a second sidewall angle from the second sidewall data; and
    determining a second sidewall quality based on the second sidewall angle data.

16. The method of claim 15, further comprising the step of creating a top-down image of the part via a camera positioned between the first laser and the second laser.

17. The method of claim 15, further comprising the step of determining a centerline of the part and a width of the part so as to simplify determination of the first sidewall angle data and second sidewall angle data.

18. The method of claim 17, further comprising the step of determining a centerline deviation.

19. The method of claim 15, further comprising the steps of generating raw data from the reflected first light signal and the reflected second light signal, filtering the raw data, and generating the first portion data and the second portion data from the filtered data.

20. A system for inspecting a part, the system comprising:
    a first laser that transmits a first light signal to the part so that the first light signal reflects off a first sidewall of the part;
    a first sensor that receives the reflected first light signal;
    a second laser spaced from the first laser, wherein the second laser transmits a second light signal to the part so that the second light signal reflects off a second sidewall of the part;
    a second sensor spaced from the first sensor, wherein the second sensor receives the reflected second light signal;
    a controller communicatively coupled with the first laser, the first sensor, the second laser, and the second sensor, wherein the controller:
    generates first portion data representative of a first portion of a part profile from the reflected first light signal;
    generates first derivative data representative of a first derivative of the first portion from the first portion data;
    generates second derivate data representative of a second derivative of the first portion from the first derivative data;
    determines first sidewall data representative of the first sidewall from the first portion data according to the first derivative data and the second derivative data;
    generates first sidewall angle data representative of a first sidewall angle from the first sidewall data;
    determines a first sidewall quality based on the first sidewall angle data;
    generates second portion data representative of a second portion of the part profile from the reflected second light signal;
    generates first derivative data representative of a first derivative of the second portion from the second portion data;
    generates second derivative data representative of a second derivative of the second portion from the first derivative data of the second portion;
    determines second sidewall data representative of the second sidewall from the second portion data according to the first derivative data of the second portion and the second derivative data of the second portion;
    generates second sidewall angle data representative of a second sidewall angle from the second sidewall data; and determines a second sidewall quality based on the second sidewall angle data;
a camera positioned between the first laser and second laser, wherein the camera creates a top-down image of the part; and
a calibration standard shiftable between a stored position and a calibration position, wherein the controller further determines a calibration of the system via the calibration standard.

* * * * *